United States Patent [19]

Reuben

[11] Patent Number: 4,857,459

[45] Date of Patent: Aug. 15, 1989

[54] STAIN FOR ACID-FAST BACILLI

[75] Inventor: Jayakumar Reuben, Baltimore, Md.

[73] Assignee: Becton, Dickinson and Company, Franklin Lakes, N.J.

[21] Appl. No.: 34,237

[22] Filed: Apr. 6, 1987

[51] Int. Cl.⁴ .................... C12Q 1/04; C12N 1/20; C12R 1/32
[52] U.S. Cl. .................... 435/34; 435/252.1; 435/253.1; 435/863
[58] Field of Search ............ 435/29, 34, 253, 252.1, 435/253.1, 863

[56] References Cited

U.S. PATENT DOCUMENTS

| | | | |
|---|---|---|---|
| 4,489,158 | 12/1984 | Straus | 435/34 X |
| 4,575,484 | 3/1986 | Straus | 435/34 X |
| 4,692,412 | 9/1987 | Livingston et al. | 435/253 |

*Primary Examiner*—David M. Naff
*Attorney, Agent, or Firm*—Mary Allen

[57] ABSTRACT

Acid-fast bacilli are stained with a primary stain that does not require heating and then with a decolorizing counter-stain that does not require a separate acid or alcohol decolorization step. The primary stain includes basic fuchsin, ethyl alcohol, isopropyl alcohol, phenol and water. The counter-stain includes methylene blue, ethyl alcohol, potassium hydroxide, glycerol, glacial acetic acid, polyvinylpyrrolidone and water.

4 Claims, No Drawings

STAIN FOR ACID-FAST BACILLI

BACKGROUND OF THE INVENTION

1. Field of the Invention

The present invention relates to a staining system for acid-fast bacilli. More particularly, the present invention relates to a quick stain for acid-fast bacilli which does not require a separate decolorization step utilizing an acid or alcohol.

2. Prior Art

The lipid containing cell walls of mycobacteria, such as *M. tuberculosis,* have the unique characteristic of binding carbolfuchsin stain so tightly that they resist destaining with strong decolorizing agents such as alcohol and strong acids. Thus, the term "acid-fast" has been used to describe a carbolfuchsin staining reaction for certain types of bacilli, such as mycobacteria which resists destaining by acids or alcohol. The acid-fast staining reaction of mycobacteria, along with their unique beaded and slightly curved shape, is a valuable aid in the early detection of infection and monitoring of therapy. The finding of acid-fast bacilli in the sputa or other mycobacteriological specimens is considered presumptive evidence of active tuberculosis and is sufficient to initiate therapy.

The present invention is an improvement in the types of acid-fast staining generally referred to as the Ziehl-Neelsen or "hot staining" method and the Kinyoun or "cold staining" method. For either method, a sample of sputum or other suitable mycobacteriological specimens, is used for preparing a culture. Preliminary digestion of the samples with pancreatin, typsin, dithiothreitol or other mucolytic substances increases the probability of isolating significant pathogenic bacteria. Since most of the bacteria found in acute pneumonia grow well on blood agar, this is the medium of choice. Inoculated plates are incubated for 18 to 24 hours and examined. Typical colonies are picked and stained with a gram stain for tentative identification of those organisms susceptible to gram staining.

In suspected cases of tuberculosis acid-fast staining techniques are used, since mycobacteria and other acid-fast organisms cannot be stained by gram stain. Smears are prepared in the same manner as for the gram stain on new slides. Slides are then treated by the Ziehl-Neelsen method or the Kinyoun method.

In the Ziehl-Neelsen method a carbolfuchsin stain is first prepared. The carbolfuchsin stain contains 0.3 grams of basic fuchsin, 10.0 milliliters of ethyl alcohol, and 90 milliliters of 5% aqueous solution of phenol. The carbolfuchsin stain is applied to the slide smears for 5 minutes, applying enough heat for gentle steaming. The stain is not permitted to evaporate and more stain is added as needed. The slides are then cooled and rinsed in water. The slides are then decolorized in a solution of 95% ethyl alcohol that contains 3% by volume of concentrated hydrocloric acid. The decolorizing solution is added until no more carbolfuchsin stain comes off. The slides are washed in tap water and are then counter-stained with a methylene blue solution for 1-2 minutes. The methylene blue solution contains 0.3 grams of methylene blue (90% dye content) and 100 ml of distilled water. The slides are then washed, dried and examined.

In the Kinyoun method the same counter-staining and methylene blue treatments are used as in the Ziehl-Neelsen method. The Kinyoun carbolfuchsin stain, however, contains 4 grams of basic fuchsin, 8 milliliters of liquefied phenol, 20 milliliters of ethyl alcohol (95%) and 100 milliliters of water. In the Kinyoun method the slide is fixed gently with heat and is then stained with the Kinyoun carbolfuchsin stain for 5 minutes without heating. The washing, decolorizing and counter-staining steps are the same as in the Ziehl-Neelsen method.

Numerous attempts have been made to minimize the time duration and number of steps involved in the Ziehl-Neelsen method and the Kinyoun method. In particular, it would be desirable to eliminate the acid decolorization step prior to counter-staining with methylene blue. None of the methods heretofore provided, however, have performed satisfactorily.

Accordingly, it is a primary object of the present invention to provide a quick acid-fast staining method which does not require a decolorizing step utilizing acid or alcohol. It is another object of the present invention to provide an acid-fast staining method which can be accomplished in less than about 10 minutes. It is another object of the present invention to provide a primary stain which can be utilized for acid-fast staining techniques which does not require heating.

These and other objects will become more apparent from the following description of the invention.

SUMMARY

The present invention is directed to providing a primary carbolfuchsin stain for use in acid-fast staining methods which does not require heating and which can be counter-stained with a secondary methylene blue stain without requiring a separate acid or alcohol decolorization step. In a preferred embodiment, the primary carbolfuchsin stain contains 2.0 grams of basic fuchsin (preferably C.I.42510), 17.5 milliliters of ethyl alcohol (95%), 1.0 milliliters of isopropyl alcohol, 7.5 grams of phenol crystals and 90 milliliters of distilled water. The primary stain is applied to a smear on a slide for 5 minutes without the requirement for heating. The smear is then rinsed with running tap water and is counter-stained with a combination decolorizer and counter-stain for 2.5 to 3 minutes. In the preferred embodiment, the decolorizing counter-stain contains 0.225 grams of methylene blue, 22.5 milliliters of ethyl alcohol, 10 ml of glycerol, 0.01 grams of potassium hydroxide, 4.5 milliliters of glacial acetic acid, 0.00001 milliliters of polyvinylpyrolidone and sufficient water to make up to 100 milliliters.

After the smear on the slide is rinsed thoroughly and after air drying, the slide may be observed under a microscope for signs of acid-fast staining of mycobacteria.

Further details of the staining method and the primary stain and decolorizing counter stain of the invention will become more apparent from the following detailed description.

DETAILED DESCRIPTION OF THE INVENTION

In accordance with the present invention, a two-step acid-fast staining method is provided. The staining method is quick, i.e. less than about 10 minutes, and does not separate a decolorizing step utilizing a concentrated acid in alcohol. The staining method of the present invention utilizes a primary stain having the ingredients indicated in Table 1 hereinbelow at the indicated relative range of usage.

TABLE 1

| Ingredient | Level of Usage |
| --- | --- |
| Basic fuchsin (preferably C.I. 42510) | 1.75–2.25 gram |
| Ethyl alcohol (95%) | 16–18.5 milliliter |
| Isopropyl alcohol | 0.975–1.025 milliliter |
| Phenol crystals | 7.2–7.8 grams |
| Distilled water | q.s. to 100 milliliters |

The primary stain is preferably prepared in accordance with the following sequence of steps:

a. Add appropriate amounts of basic fuchsin, preferably C.I.42510, to ethyl alcohol and mix thoroughly. Allow the solution to stand at room temperature, periodically shaking the solution, for 48 hours.

b. Add the isopropyl alcohol to the solution and mix well. Allow to stand at room temperature for one hour.

c. Filter the solution through a 1.0 micron filter equipped with a prefilter.

d. Add appropriate amounts of phenol crystals to distilled water. Mix thoroughly until all of the phenol crystals are fully dissolved.

Add the aqueous solution of phenol to the dye/ethanol mixture. Mix thoroughly and allow the solution to stand for 4 hours. Add water to bring the solution volume to 100 ml.

Filter the solution through a 1.0 micron filter equipped with a prefilter, twice.

The quick acid-fast staining method of the present invention utilizes a unique decolorizing counter stain which serves the dual purpose of decolorizing and counter-staining a slide smeared with mycobacteriological samples and stained with carbolfuchsin. The decolorizing counter stain used for the combination steps of decolorizing and counter-staining contains the following ingredients at the indicated relative range of usage as set forth in Table 2.

TABLE 2

| Ingredients | Level of Usage |
| --- | --- |
| Methylene blue | 0.2–0.25 gram |
| Ethyl alcohol | 20–25 milliliter |
| Potassium hydroxide | 0.0075–0.0125 gram |
| Glycerol | 9.5–10.5 milliliters |
| Glacial acetic acid | 4–5 milliliter |
| Polyvinylpyrrolidone (0.01 V/V% solution) | 0.05–0.1 milliliter |
| Distilled water | q.s. to 100 milliliters |

The counterstain is prepared in accordance with the following procedure:

a. Place the required amount of ethyl alcohol in a suitable container.

b. Add the required amount of methylene blue and mix thoroughly to dissolve.

c. Add the required amount of a potassium hydroxide solution (prepared separately) and mix well.

d. Filter the above base reagent through a 1.0 micron filter equipped with a prefilter.

e. Add the required amount of glacial acetic acid and mix well.

f. Add the required amount of glycerol and mix well.

g. Add the required amount of the aqueous solution of PVP (prepared separately), and mix thoroughly. Add water to bring the solution volume to 100 ml.

h. Let the reagent stand for 2–3 hours at room temperature. Filter the reagent twice with a 1.0 micron filter.

Glacial acetic acid (4.5 ml.), is used as one of the decolorizers, instead of HCl in the counterstain, because it is a weak acid. When mixed with appropriate amounts of 95% ethyl alcohol, resulting mixture of acid and alcohol provides an optimum degree of decolorization. Other acids decolorize the less acid fast bacilli, specially some of the Atypical Mycobacteria (M. fortuitum, M. chelonei, M. smegmatis and others). The staining formulations yield superior staining reactions for the MOTT (Mycobacteria Other Than Tuberculosis), as compared to Ziehl-Neelsen, Kinyoun, or the Microdiagnostics stain.

Polyvinylpyrrolidone is added to the secondary stain for two reasons; (1) as a wetting agent, to increase the ability of the decolorizing counter stain to clear up the smear of phenol-induced primary stain precipitates and impurities and (2) to provide a deeper bluish hue to the background. Amounts of polyvinylpyrrolidone in excess of 1 ml. of a 0.01 (V/V %) aqueous solution will result in thickening of the counterstain/decolorizer reagent, giving less than optimal performance. Glycerol is in the decolorizing counter stain as a stabilizing agent.

The presence of ethyl alcohol in the decolorizing counter stain is important. Without the required amount of ethyl alcohol, the primary stain precipitates are left on the smear making it unsuitable for microscopy. Ethyl alcohol in combination with Glacial acetic acid is required to decrease the time for counterstaining to about 2.5 to 3 min. Ziehl-Neelsen and Kinyoun methods require multiple decolorization steps i.e., a minimum of 2 to 3 separate washings with acid alcohol and water, before applying the counterstain.

Most clinical smears contain significant amounts of NaOH. The high amounts of alkali present in the smears, tends to "burn up" the smears, during the primary staining process. Primary stains which contain significant amounts of Basic Fuchsin/Carbolic acid (with or without surfactants such as Tergitol), when left in contact with smears containing high alkali, scorch the smears to a significant degree; Glacial acetic acid by itself is unable to remove all of the scorched stain precipitates, even after 5 minutes. In the present invention the amount of Basic Fuchsin in the primary stain is reduced to about 2.0 g. instead of the 4.0 g. present in the Kinyoun method. Amounts less than about 2.0 g. of Basic Fuchsin, without the application of heat, is too dilute to effectively stain the Mycobacteria. The combination of 2.0 g. of Basic Fuchsin (C.I. 42510) in 17.5 ml. of 95% ethyl alcohol and a final concentration of phenol of from about 6.3 percent to about 6.7 percent of the primary stain, appears to provide a primary stain that results in acceptable degree of dye penetration into the cells, without the undesirable stain precipitate and scorching of the smears, specially the ones prepared from concentrated clinical specimens. All percentages used herein are by weight, unless otherwise indicated.

The secondary stain provides optimum results only when used with the primary stain of the invention, and when the recommended time durations are adhered to.

In usage, a slide is prepared in accordance with known technology used to prepare sputum or other specimen slides for the Ziehl-Neelsen method or the Kinyoun method. The primary stain of the invention is then applied to the smear on the slide and the slide is incubated for a period of from about 4 to about 6 minutes. The application of the primary stain is at ambient temperature and no heating is required. The smear is then rinsed with running tap water for a period of from about 30 seconds to about 1 minute. The smear is then decolorized and counter-stained with the secondary stain prepared in accordance with Table 2 and the slide is incubated for a period of from about 2 to about 4 minutes. The smear is then thoroughly rinsed and after air drying is ready to be observed under a microscope in accordance with procedures known for use with the Ziehl-Neelsen and Kinyoun methods observed under a microscope in accordance with procedures known for use with the Ziehl-Neelsen and the Kinyoun methods.

What is claimed:

1. A staining system for acid-fast, bacilli comprising a primary stain and a separate decolorizing counter-stain wherein
said primary stain is an aqueous solution containing for each 100 ml of solution the following constituents:
from 1.75 to 2.25 gm basic fuchsin;
from 16 to 18.5 ml ethyl alcohol;
from 0.925 to 1.025 ml isopropyl alcohol; and
from 7.2 to 7.8 gm phenol; and
said separate decolorizing counter-stain is an aqueous solution containing for each 100 ml of solution the following constituents
from 0.2 to 0.25 gm methylene blue;
from 20 to 25 ml ethyl alcohol;
from 0.0075 to 0.0125 gm potassium hydroxide;
from 9.5 to 10.5 ml glycerol
from 4 to 5 ml acetic acid; and
from 0.05 to 0.1 polyvinylpyrrolidone (0.01 V/V % solution).

2. A staining system in accordance with claim 1 wherein said basic fuchsin of said primary stain is C.I. 42510 basic fuchsin.

3. A method for staining a slide in preparation for microscopic observation of acid-fast bacili comprising:
preparing a slide with a suspected mycobacteriological sample;
applying a primary stain to the slide wherein said primary stain is an aqueous solution containing for each 100 ml of solution the following constituents:
from 1.75 to 2.25 gm basic fuchsin;
from 16 to 18.5 ml ethyl alcohol;
from 0.925 to 1.025 ml isopropyl alcohol; and
from 7.2 to 7.8 gm phenol;
incubating the slide for a first period of about to about 6 minutes;
rinsing the slide;
applying a decolorizing counter-stain to the slide wherein the decolorizing counter-stain is an aqueous solution having for each 100 ml of solution the following constituents:
from 0.2 to 0.25 gm methylene blue;
from 20 to 25 ml ethyl alcohol;
from 0.0075 to 0.0125 gm potassium hydroxide;
from 9.5 to 10.5 ml glycerol
from 4 to 5 ml acetic acid; and
from 0.05 to 0.1 ml polyvinylpyrrolidone 0.01 V/V % solution
inoculating the slide for a second period of from about 2 to about 4 minutes; and
rinsing the slide.

4. A method in accordance with claim 3 wherein said first incubation and said second incubation take plate at ambient temperature.

* * * * *